(12) United States Patent
Wang et al.

(10) Patent No.: US 11,284,925 B2
(45) Date of Patent: Mar. 29, 2022

(54) INTERNAL FIXATION SYSTEM OF SPINE POSTERIOR SCREW-PLATE

(71) Applicant: Central South University Xiangya Hospital, Changsha (CN)

(72) Inventors: Xiyang Wang, Changsha (CN); Zheng Liu, Hengyang (CN); Yilu Zhang, Changsha (CN); Yunqi Wu, Kunming (CN); Zhenchao Xu, Yiyang (CN); Weiwei Li, Changsha (CN); Zhicheng Sun, Yiyang (CN); Yilin Wang, Changsha (CN); Zhen Zhang, Chongqing (CN); Dingchao Rong, Yongzhou (CN); Hongru Ye, Changsha (CN); Xiao Xiao, Changsha (CN)

(73) Assignee: Central South University Xiangya Hospital, Changsha (CN)

( * ) Notice: Subject to any disclaimer, the term of this patent is extended or adjusted under 35 U.S.C. 154(b) by 188 days.

(21) Appl. No.: 16/541,151

(22) Filed: Aug. 15, 2019

(65) Prior Publication Data
US 2021/0045781 A1 Feb. 18, 2021

(51) Int. Cl.
*A61B 17/70* (2006.01)
*A61B 17/88* (2006.01)
*A61B 17/80* (2006.01)

(52) U.S. Cl.
CPC ...... *A61B 17/7059* (2013.01); *A61B 17/7002* (2013.01); *A61B 17/7043* (2013.01); *A61B 17/8033* (2013.01); *A61B 17/8802* (2013.01)

(58) Field of Classification Search
CPC ............ A61B 17/7049; A61B 17/7058; A61B 17/7059; A61B 17/7061; A61B 17/7062; A61B 17/7068
See application file for complete search history.

(56) References Cited

U.S. PATENT DOCUMENTS

| | | | | |
|---|---|---|---|---|
| 5,437,672 A | * | 8/1995 | Alleyne | A61B 17/00 606/279 |
| 9,526,533 B1 | * | 12/2016 | Aranibar | A61B 17/7011 |
| 10,952,856 B2 | * | 3/2021 | Freese | A61B 17/7043 |
| 2009/0326592 A1 | * | 12/2009 | Butler | A61B 17/7058 606/286 |
| 2010/0174315 A1 | * | 7/2010 | Scodary | A61B 17/7052 606/248 |
| 2011/0060367 A1 | * | 3/2011 | Stauber | A61B 17/7052 606/250 |
| 2012/0158060 A1 | * | 6/2012 | Abrahams | A61B 17/7065 606/248 |

(Continued)

*Primary Examiner* — Nicholas W Woodall
(74) *Attorney, Agent, or Firm* — McClure, Qualey & Rodack, LLP

(57) ABSTRACT

The invention provides the internal fixation system of spine posterior screw-plate, including the vertebral plate. The vertebral plate is curved, its internal cambered surface directly faces the spine, and external cambered surface of vertebral plate is equipped with a reinforcing rib. The vertebral plate is set with the perforative injecting hole. One side of vertebral plate is fixed with a fixed connecting plate, and the end of the fixed connecting plate away from the vertebral plate is set with the first regulating hole. The bottom of the fixed connecting plate on two sides of the first regulating hole is set with n-shaped caulking groove.

6 Claims, 8 Drawing Sheets

(56) References Cited

U.S. PATENT DOCUMENTS

| | | | |
|---|---|---|---|
| 2014/0052183 A1* | 2/2014 | Freese | A61B 17/0401 |
| | | | 606/248 |
| 2014/0277154 A1* | 9/2014 | Perry | A61B 17/8042 |
| | | | 606/270 |
| 2017/0265904 A1* | 9/2017 | Wolfe | A61B 17/7043 |
| 2017/0325852 A1* | 11/2017 | Chen | A61B 17/705 |
| 2021/0045780 A1* | 2/2021 | Zhu | A61B 17/7032 |

* cited by examiner

INTERNAL FIXATION SYSTEM OF SPINE POSTERIOR SCREW-PLATE

TECHNICAL FIELD

The invention involves the field of surgical medical equipment, especially the internal fixation system of spine posterior screw-plate.

BACKGROUND TECHNOLOGY

Most of the existing vertebral plate is elongated, which is fixed on both sides of the spine after operation. This method is to first place the vertebral plate against the spine, and to insert the steel nail according to position of the fixing hole of vertebral plate to fix the vertebral plate. This method is tedious to operate, and the positioning effect is poor.

Contents of the Invention

The purpose of the invention is to overcome the deficiency of the current technology and to provide the internal fixation system of spine posterior screw-plate with the reasonable structure and good use effect.

To realize the above purposes, the technical scheme which is provided by the invention is as follows: The internal fixation system of spine posterior screw-plate includes the vertebral plate. The vertebral plate is curved, its internal cambered surface directly faces the spine, and external cambered surface of vertebral plate is equipped with a reinforcing rib. The vertebral plate is set with the perforative injecting hole. One side of vertebral plate is fixed with a fixed connecting plate, and the end of the fixed connecting plate away from the vertebral plate is set with the first regulating hole. The bottom of the fixed connecting plate on two sides of the first regulating hole is set with n-shaped caulking groove. The first locating rod is embedded in the caulking groove, and the first locating rod in the caulking groove is locked by the first locking screw; the other side of the vertebral plate is hinged with the movable connecting plate through the positioning bolt, and the second locating rod is installed at the bottom of the movable connecting plate through the second locking screw. Screw-plate components are movably installed at two sides of the first locating rod and two sides of the second locating rod.

The mentioned screw-plate components include the screw, the top of screw expands to form a located block, and the top of the located block is set with the concave screw hole. The screw hole is set with the internal thread, and the located blocks on two sides of the screw hole is set with the U-shaped bracket. The end of the first locating rod and the second locating rod is supported by the bottom of corresponding bracket. The screw hole on the top of the first locating rod and the second locating rod is set with gasket and lock nut. The gasket is placed on the surface of the first locating rod and the second locating rod, and the lock nut engages with the internal thread in the screw hole.

The mentioned bottom of the movable connecting plate away from the vertebral plate is set with the n-shaped locating groove, and the locating groove fits with the second locating rod. After fitting, it is locked by the second locking screw.

The mentioned two fixed connecting plates are respectively located at two ends of one side of the vertebrate plate, and two movable connecting plates are respectively located at two ends of other side of the vertebral plate.

The mentioned fixed connecting plate is formed through extending one side of the vertebral plate.

The mentioned reinforcing rib humps on the surface of the vertebral plate in the form of "cross", the reinforcing rib extends to form a cylinder at the central intersection, and the injecting hole is distributed in a matrix on the vertebral plate.

The above scheme is used in the invention. According to the position where the spine shall be fixed, place the screw on the body on both sides of the spine, embed the end of the first locating rod and the second locating rod into the corresponding bracket, place the gaskets on the surfaces of the first locating rod and the second locating rod, and place the lock nuts into the screw hole to fix the first locating rod and the second locating rod. Make the internal cambered surface of the vertebral plate directly face the spine, align the first locating rod with a caulking groove to fit. After fitting, it is locked by a locking screw. The locking screw adopts 201821967697X regulating mechanism. According to the position of the second locating rod, rotate the movable connecting plate to make the locating groove fit with the second locating rod. After fitting, it is locked by the locking screw to complete the positioning of vertebral plate. After this scheme is adopted, the structure is reasonable, and the use effect is good. Instruction with drawings FIG. 1 is the overall structure schematic diagram of the invention.

SPECIFIC IMPLEMENTATION MODE

Figure 1:
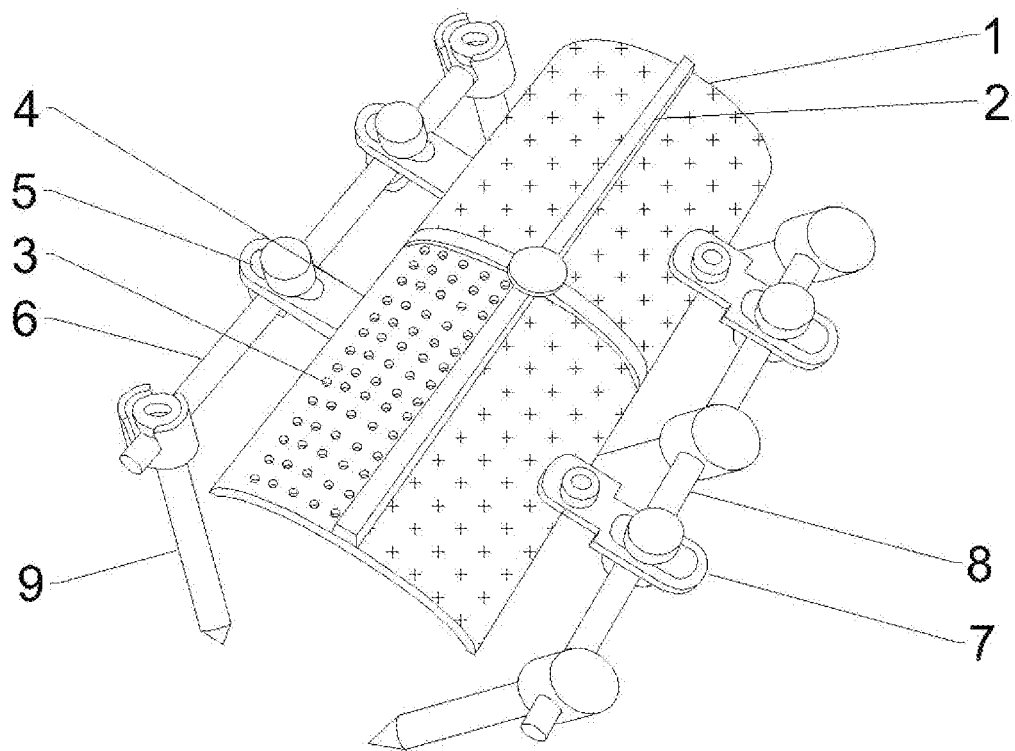
Figure 2:
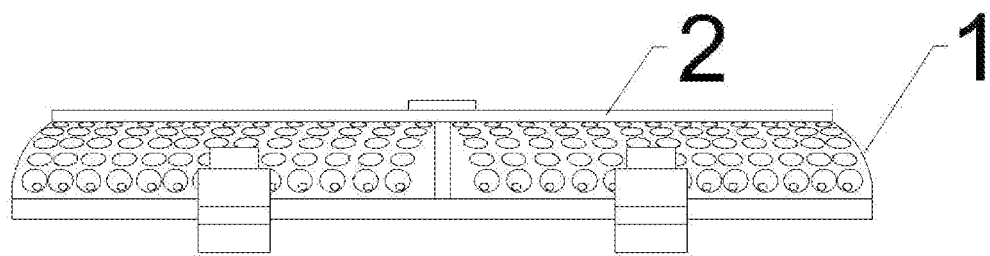
FIG. 2 is the side elevation drawing.
Figure 3:
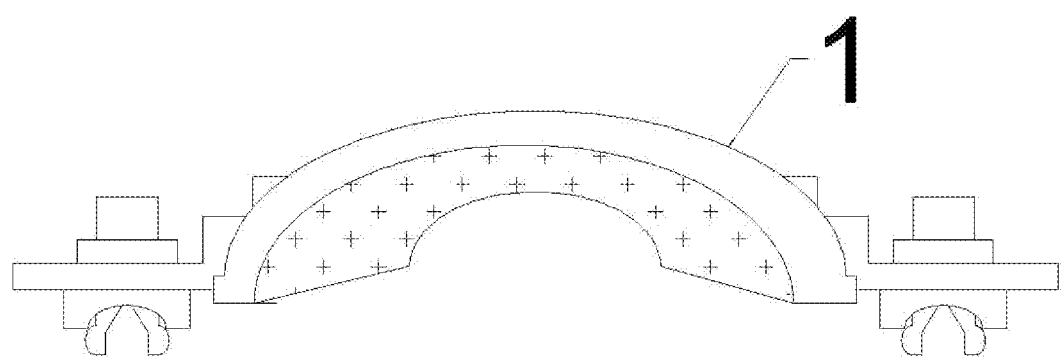
FIG. 3 is the end schematic diagram of the invention.
Figure 4:
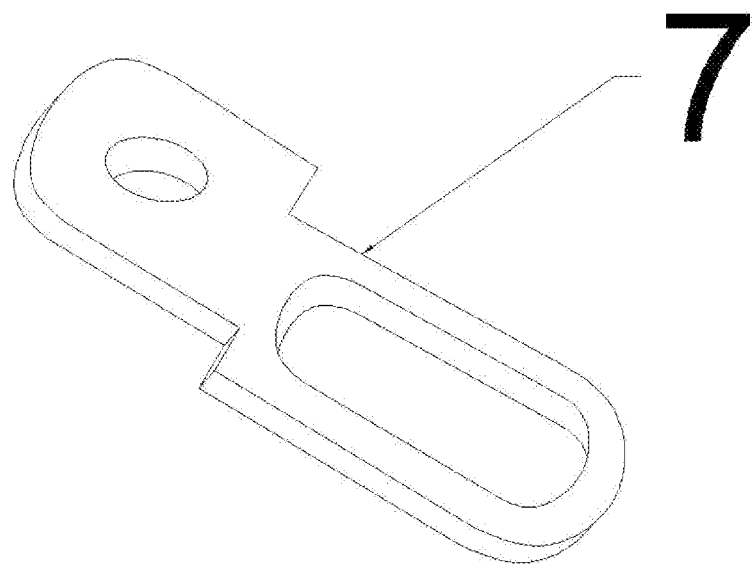
FIG. 4 is a schematic diagram of one movable connecting plate of the invention.
Figure 5:
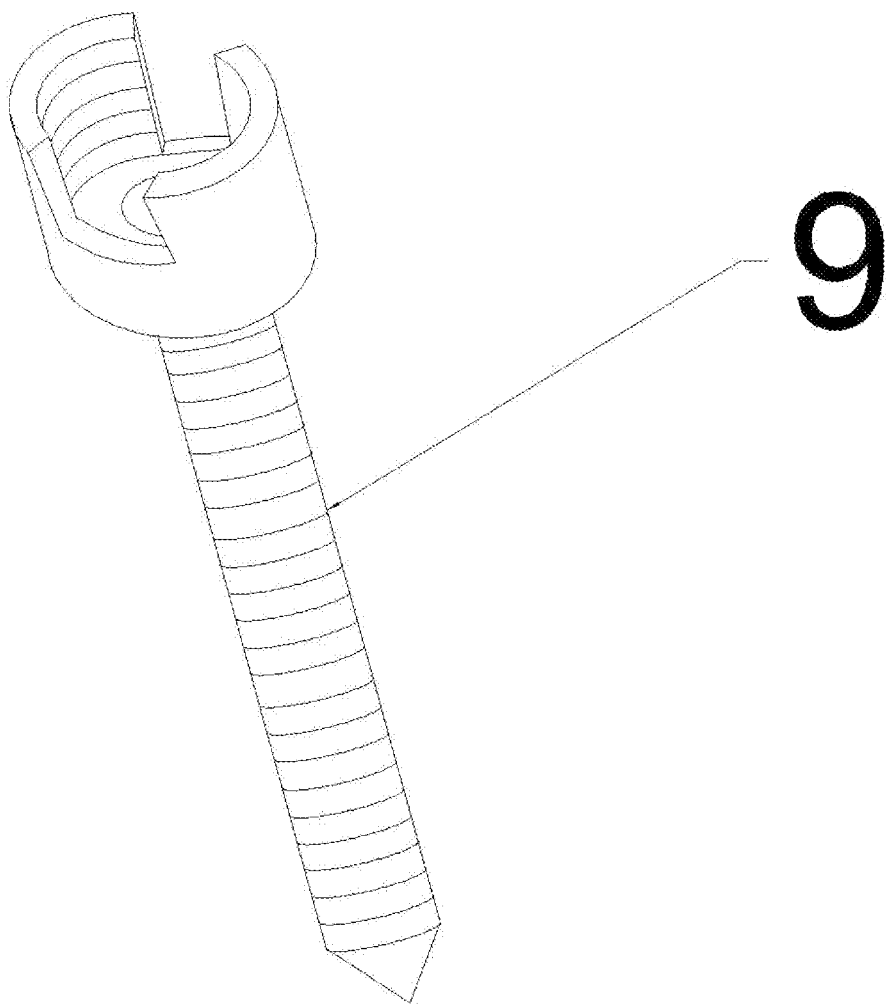
FIG. 5 is the screw schematic diagram of the invention.
Figure 6:
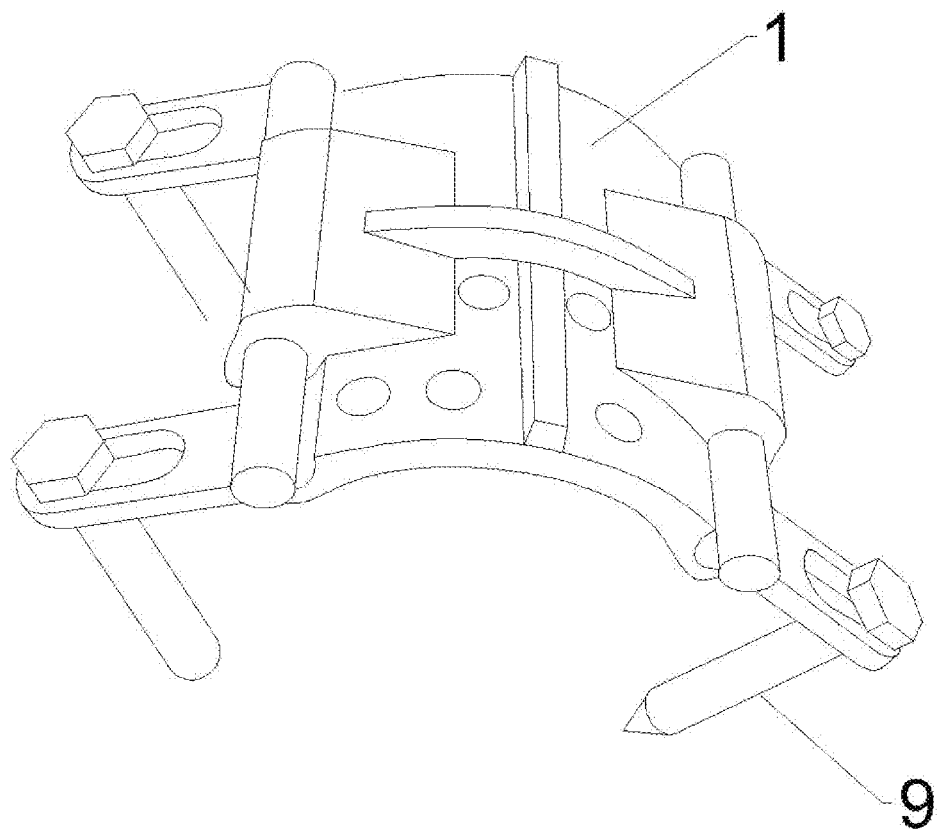
FIG. 6 is a schematic diagram of movable connecting plates on two sides of the invention.
Figure 7:
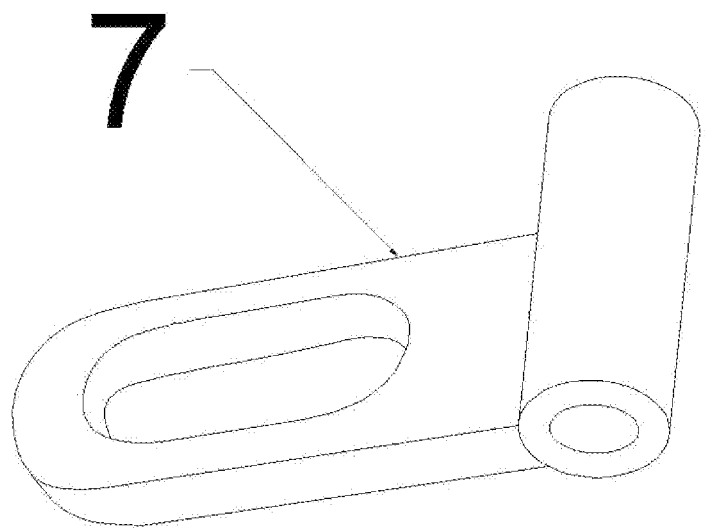
FIG. 7 is another structural diagram of movable connecting plate.
Figure 8:
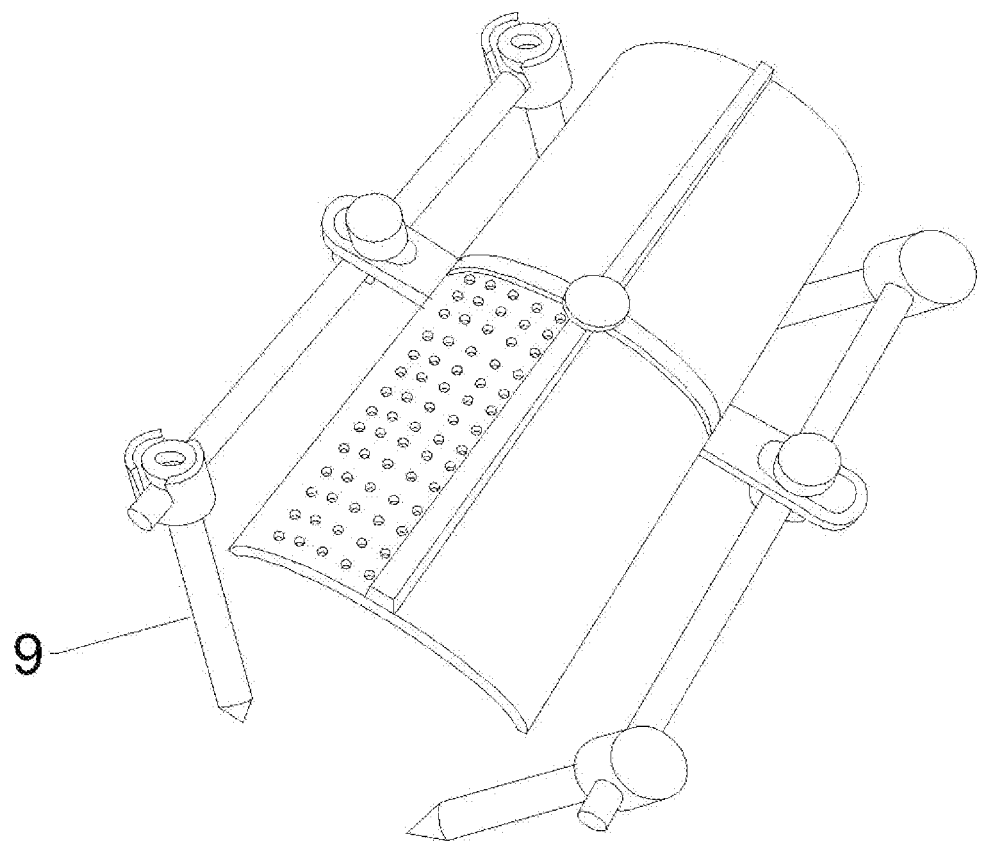
FIG. 8 is a schematic diagram of fixed connecting plates on two sides.

The invention is further described in combination with all the attached drawings, and the better embodiment of the invention is as follows:

The embodiment 1 is shown in the attached drawings 1-5. The internal fixation system of spine posterior screw-plate mentioned in the embodiment includes the vertebral plate 1. The vertebral plate 1 is curved, its internal cambered surface directly faces the spine, and external cambered surface of vertebral plate 1 is equipped with a reinforcing rib 2. The vertebral plate 1 is set with the perforative injecting hole 3. The reinforcing rib 2 humps on the surface of the vertebral plate 1 in the form of "cross", the reinforcing rib 2 extends to form a cylinder at the central intersection, and the injecting hole 3 is distributed in a matrix on the vertebral plate 1. The end of the fixed connecting plate 4 away from the vertebral plate 1 is set with the first regulating hole 5. The bottom of the fixed connecting plate 4 on two sides of the first regulating hole 5 is set with n-shaped caulking groove where the first locating rod 6 is embedded in, and the first locating rod 6 in the caulking groove is locked by the first locking screw; the other side of the vertebral plate 1 is hinged with the movable connecting plate 7 through the positioning bolt. Two fixed connecting plates 4 are located at two ends of one side of the vertebral plate 1 respectively, and two movable connecting plates 7 are located at two ends of the other side of the vertebral plate 1 respectively. The second locating rod 8 is installed at the bottom of the movable connecting plate 7 through the second locking screw. The bottom of the movable connecting plate 7 away from the vertebral plate 1 is set with the n-shaped locating groove, and the locating groove fits with the second locating rod 8. After fitting, it is locked by the second locking screw. Two ends of the first locating rod 6 and the second locating rod 8 are installed with screw-plate components. The screw-plate components include the screw 9, the top of screw 9 expands to form a located block, and the top of the located block is set with the concave screw hole. The screw hole is set with the internal thread, and the located blocks on two sides of the screw hole is set with the U-shaped bracket. The end of the first locating rod 6 and the second locating rod 8 is supported by the bottom of corresponding bracket. The screw hole on the top of the first locating rod 6 and the second locating rod 8 is set with gasket and lock nut. The gasket is placed on the surface of the first locating rod 6 and the second locating rod 8, and the lock nut engages with the internal thread in the screw hole.

In this embodiment, place the screw on the body on both sides of the spine according to the position where the spine shall be fixed, then embed the end of the first locating rod and the second locating rod into the corresponding bracket, place the gaskets on the surfaces of the first locating rod and the second locating rod, and place the lock nuts into the screw hole to fix the first locating rod and the second locating rod. Make the internal cambered surface of the vertebral plate directly face the spine, align the first locating rod with a caulking groove to fit. After fitting, it is locked by a locking screw. The locking screw adopts 201821967697X regulating mechanism. According to the position of the second locating rod, rotate the movable connecting plate to make the locating groove fit with the second locating rod. After fitting, it is locked by the locking screw to complete the positioning of vertebral plate. After this scheme is adopted, the structure is reasonable, and the use effect is good.

The embodiment 2is shown in the attached drawings 6 and 7. A fixed connecting plate may be used in this scheme, which is convenient for special patients.

The embodiment 3 is shown in the attached drawings 8. Two movable connecting plates of hinged joint may be used in this scheme.

The above embodiments are only better embodiments of the invention and don't limit the implementation scope of the invention, so the changes that are made according to the shape and principle of the invention shall be covered in the protection scope of the invention.

We claim:

1. An internal fixation system of a spine posterior screw-plate, comprising:
    a curved vertebral plate (1) having:
        an internal cambered surface of the curved vertebral plate (1) directly facing a spine;
        an external cambered surface opposite the internal cambered surface and having reinforcing ribs (2); and
        one or more injecting holes (3);
    one or more fixed connecting plates (4) attached on either side of the curved vertebral plate (1), wherein an end of each of the one or more fixed connecting plates (4) away from the curved vertebral plate (1) is provided with one or more first regulating holes (5), a bottom portion of each of the one or more fixed connecting plates (4) on both sides of the one or more first regulating holes (5) is provided with an n-shaped caulking groove;
    a first locating rod (6) extending longitudinally off one side of the curved vertebral plate (1) and passes through the caulking grooves, wherein the first locating rod (6) in the caulking grooves is locked by first locking screws;
    one or more movable connecting plates (7) hinged on another side of the curved vertebral plate (1) through positioning bolts,
    a second locating rod (8) extending longitudinally off an opposite side of the curved vertebral plate (1) and passing through the caulking grooves through second locking screws; and
    screw-plate components movably installed at both sides of the first locating rod (6) and both sides of the second locating rod (8).

2. The internal fixation system of a spine posterior screw-plate according to claim 1, wherein the screw-plate components include one or more screws (9), a top portion of at least one of the one or more screws (9) expands to form a located block, and a top portion of the located block is provided with a concave screw hole with internal threads, and the located blocks on both sides of the screw hole is provided with U-shaped indentations, an end portion of the first locating rod (6) and an end portion of the second locating rod (8) are supported by the bottom portions of the corresponding U-shaped indentations at the screw holes of the one or more screws (9), a top portion of the first locating rod (6) and a top portion of the second locating rod (8) are provided with one or more gaskets and one or more lock nuts; the one or more gaskets are placed on a surface of the first locating rod (6) and a surface of the second locating rod (8), and the one or more lock nuts engages with the internal threads in the screw holes at the one or more screws (9).

3. The internal fixation system of a spine posterior screw-plate according to claim 1, wherein bottom portions of ends of the one or more movable connecting plates (7) away from the curved vertebral plate (1) are provided respectively with an n-shaped locating groove, which is used to fix the second locating rod (8), and after fitting, the second locating rod (8) is locked by the second locking screws.

4. The internal fixation system of a spine posterior screw-plate according to claim 1, wherein a number of the fixed connecting plates (4) located on both ends of one side of the curved vertebral plate (1) is two, and a number of the movable connecting plates (7) located at both ends at another side of the curved vertebral plate (1) is two.

5. The internal fixation system of a spine posterior screw-plate according to claim 1, wherein the one or more fixed connecting plates (4) are formed through extending one side of the curved vertebral plate (1).

6. The internal fixation system of a spine posterior screw-plate according to claim 1, wherein the reinforcing ribs (2) hump on the external cambered surface of the curved vertebral plate (1) in a form of "a cross", a cylinder is formed at an intersection of the reinforcing ribs (2), and the one or more injecting holes (3) are distributed in a matrix on the curved vertebral plate (1).

* * * * *